United States Patent [19]

Shimada et al.

[11] Patent Number: 5,047,590
[45] Date of Patent: Sep. 10, 1991

[54] DINITRO COMPOUNDS, DIAMINO COMPOUNDS AND TRIAMINE COMPOUNDS AND PREPARATION METHODS THEREOF

[75] Inventors: Tomoyuki Shimada, Numazu; Masaomi Sasaki, Susono; Tamotsu Aruga, Mishima, all of Japan

[73] Assignee: Ricoh Company, Ltd., Tokyo, Japan

[21] Appl. No.: 530,166

[22] Filed: May 29, 1990

[30] Foreign Application Priority Data

May 31, 1989 [JP] Japan ............................ 1-140107
May 31, 1989 [JP] Japan ............................ 1-140108

[51] Int. Cl.$^5$ ............................................ C07C 211/54
[52] U.S. Cl. .................................... 564/309; 564/307; 564/308; 564/433; 564/434
[58] Field of Search .................... 564/433, 434, 307

[56] References Cited

U.S. PATENT DOCUMENTS 3,180,730  4/1965  Klupfel et al. ..................... 430/74
3,251,881  5/1966  Susi et al. ......................... 564/434
3,265,496  8/1966  Fox et al. .......................... 430/73
4,588,666  5/1986  Stolka et al. ..................... 564/309

FOREIGN PATENT DOCUMENTS 3810522  3/1988  Fed. Rep. of Germany .
1134354  1/1984  Japan .

Primary Examiner—Richard L. Raymond
Assistant Examiner—Shailendra Kumar
Attorney, Agent, or Firm—Oblon, Spivak, McClelland, Maier & Neustadt

[57] ABSTRACT

Compounds having formula (I), which are useful as starting or intermediate materials for preparing organic photoconductive materials, or as organic photoconductive materials:

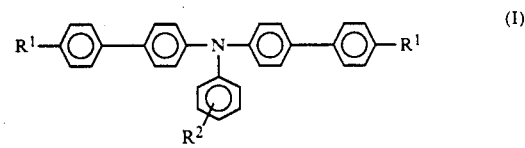

(I)

wherein $R^1$ is a nitro group, an amino group or a diphenylamino group which may have a substituent; and $R^2$ is hydrogen or an alkyl group having 1 to 6 carbon atoms, and methods of preparing the above compounds are disclosed.

10 Claims, 8 Drawing Sheets

DINITRO COMPOUNDS, DIAMINO COMPOUNDS AND TRIAMINE COMPOUNDS AND PREPARATION METHODS THEREOF

BACKGROUND OF THE INVENTION

1. Field of the Invention

The present invention relates to dinitro compounds and diamino compounds, and in particular, to dinitro compounds and diamino compounds which are useful as starting or intermediate materials for preparing organic photoconductive materials for use in electrophotography, and preparation methods thereof. The present invention further relates to triamine compounds which are useful as organic photoconductive materials for use in electrophotography and a preparation method thereof.

2. Discussion of Background

A two-layered type electrophotographic photoconductor, one type of electrophotographic photoconductors, is widely used in the field of electrophotography. As conventionally known, the above-mentioned two-layered type electrophotographic photoconductor is constructed in such a manner that (i) a charge generation layer comprising a charge generating material capable of generating charge carriers when exposed to light, and (ii) a charge transport layer comprising a charge transporting material capable of efficiently injecting the above-mentioned charge carriers in the charge transport layer and transporting the same, are successively overlaid on an electroconductive support.

It is conventionally known that various azo compounds are effective as the charge generating material in the above-mentioned two-layered type electrophotographic photoconductor. For example, benzidine type bisazo compounds in Japanese Laid-Open Patent Applications 47-37543 and 52-55643; stilbene type bisazo compounds in Japanese Laid-Open Patent Application 52-8832; diphenylhexatoriene type bisazo compounds in Japanese Laid-Open Patent Application 58-222152; and diphenylbutadiene type bisazo compounds in Japanese Laid-Open Patent Application 58-222153 are well known.

On the other hand, various kinds of the charge transporting materials, which are to be contained in the charge transport layer of the two-layered type electrophotographic photoconductor in the electrophotographic process, are also conventionally proposed. For example, poly-N-vinylcarbazole and triphenylamine compounds are disclosed in U.S. Pat. No. 3,180,730; and benzidine compounds are disclosed in U.S. Pat. No. 3,265,496, Japanese Patent Publication 39-11546 and Japanese Laid-Open Patent Application 53-27033.

The above-mentioned electrophotographic process is one of the image forming processes, in which the surface of the photoconductor is charged uniformly in the dark of a predetermined polarity, for instance by corona charge. The uniformly charged photoconductor is exposed to a light image to selectively dissipate the electrical charge of the exposed areas, so that a latent electrostatic image is formed on the photoconductor. The thus formed latent electrostatic image is developed by a developer to a visible image.

Fundamental characteristics required for the photoconductor in such an electrophotographic process are: (1) chargeability to an appropriate potential in the dark, (2) minimum dissipation of electrical charge in the dark, and (3) rapid dissipation of electrical charge when exposed to the light.

However, the conventional organic photoconductive materials do not necessarily satisfy the above electrophotographic characteristics at the same time.

SUMMARY OF THE INVENTION

Accordingly, a first object of the present invention is to provide compounds which are useful as starting or intermediate materials for preparing organic photoconductive materials for use in an electrophotographic photoconductor, and in particular, for preparing charge generating materials or charge transporting materials for use in a two-layered type electrophotographic photoconductor from which the conventional drawbacks are eliminated, or which are useful as such organic photoconductive materials.

A second object of the present invention is to provide methods of preparing the above compounds.

The aforementioned first object of the present invention can be achieved by a compound having the following formula (I):

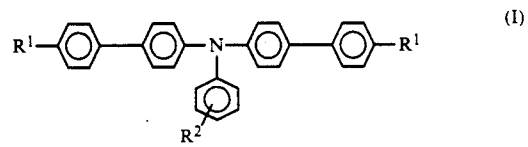

wherein $R^1$ represents a nitro group, an amino group or a diphenylamino group which may have a substituent; and $R^2$ represents hydrogen or an alkyl group having 1 to 6 carbon atoms.

In the above formula, when $R^1$ is a nitro group or an amino group, and $R^2$ is the same as defined above, the above compound can be employed as a starting or intermediate material for preparing an organic photoconductive material; and when $R^1$ is a diphenylamino group which may have a substituent, and $R^2$ is the same as defined above, the compound can be employed as an organic photoconductive material.

The above-mentioned second object of the present invention, particularly when $R^1$ in the above formula (I) is a nitro group as shown below by formula (I)-A, can be achieved by allowing 4'-halogeno-4-nitro(1,1'-biphenyl) having formula (II) to react with an amino compound having formula (III) in the following reaction scheme:

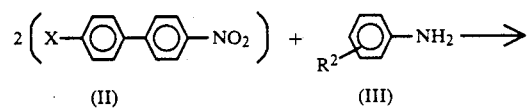

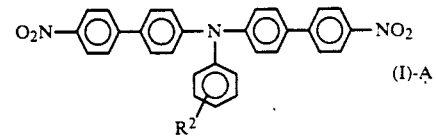

Further, when $R^1$ in the above formula (I) is an amino group as shown below by formula (I)-B, the second object of the present invention can be achieved by reducing the above compound of formula (I)-A:

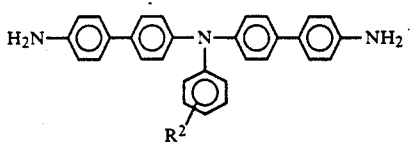

When $R^1$ is a diphenylamino group which may have a substituent, the second object of the present invention can be achieved by allowing the previously mentioned diamino compound having formula (I)-B to react with a halobenzene compound having formula (IV) in the reaction scheme shown below:

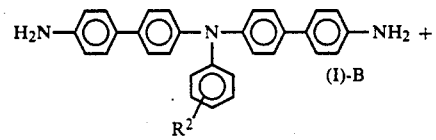

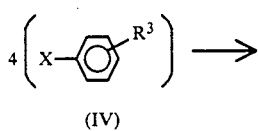

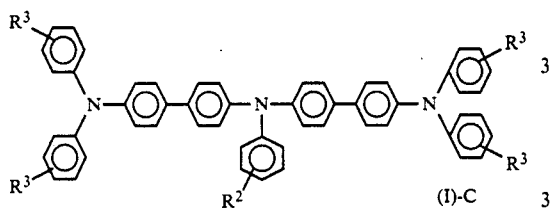

wherein $R^2$ is hydrogen or an alkyl group having 1 to 6 carbon atoms, $R^3$ is hydrogen or an alkyl group having 1 to 6 carbon atoms, and X is a halogen.

BRIEF DESCRIPTION OF THE DRAWINGS

In the figures.

DESCRIPTION OF THE PREFERRED EMBODIMENTS

Figure 1:
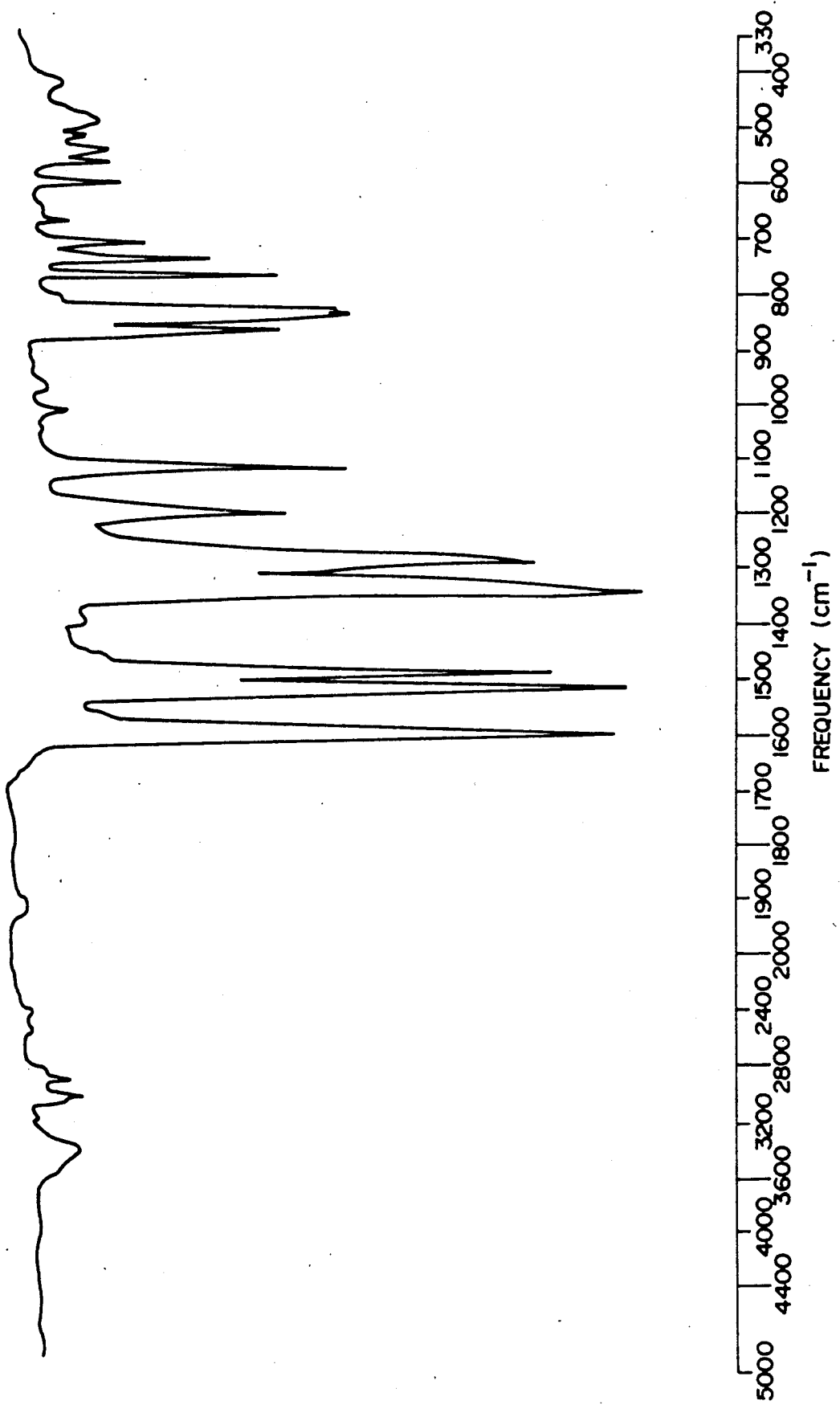
FIGS. 1 to 4 are the infrared absorption spectra of dinitro compounds and diamino compounds according to the present invention.

According to the present invention, a compound having the following formula (I), which is useful as a starting or intermediate material for preparing an organic photoconductive material or as an organic photoconductive material for use in electrophotography, is provided:

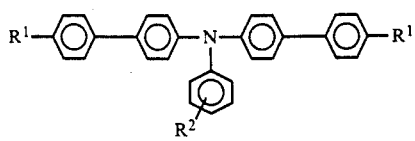

wherein $R^1$ represents a nitro group, an amino group or a diphenylamino group which may have a substituent; and $R^2$ represents hydrogen or an alkyl group having 1 to 6 carbon atoms.

In the case where $R^1$ in formula (I) is a nitro group, the compound of formula (I) is the following dinitro compound of formula (I-A):

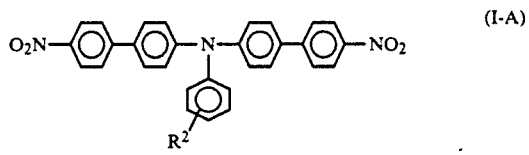

wherein $R^2$ represents the same as previously defined.

The above-mentioned dinitro compound of formula (I-A) is prepared by allowing 4'-halogeno-4-nitro(1,1'-biphenyl) having formula (II) to react with an amino compound having formula (III):

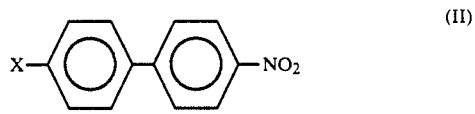

wherein X represents a halogen.

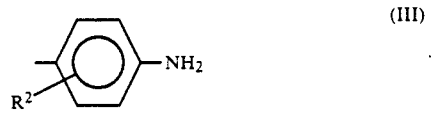

wherein $R^2$ represents the same as previously defined.

More specifically, 4'-halogeno-4-nitro(1,1'-biphenyl) of formula (II) is allowed to react with an amino compound of formula (III) in the presence of copper powder or halogenated copper and an alkali with or without a solvent. The reaction is carried out in a stream of nitrogen under application of heat, whereby the dinitro compound of formula (I-A) can be obtained. This reaction is called Ullmann reaction.

The above-mentioned alkali is added to the reaction mixture in a sufficient amount to neutralize hydrogen halogenide generated in the condensation reaction. Examples of the above alkali for use in the present invention are sodium hydroxide, potassium hydroxide, sodium carbonate and potassium carbonate.

Specific examples of the solvent for use in the above reaction are nitrobenzene, dichlorobenzene, quinoline, N,N-dimethylformamide, dimethyl sulfoxide, N-methylpyrrolidone and 1,3-dimethyl-2-imidazolidinone.

The diamino compound having formula (I)-B according to the present invention can be prepared by reducing the above-mentioned dinitro compound of formula (I)-A.

The reduction of the dinitro compound of formula (I)-A may be carried out, for example, by hydrogenation.

The above hydrogenation reaction is performed by use of a homogeneous catalyst or heterogeneous catalyst.

Examples of the homogeneous catalysts for use in the present invention are complex compounds of metallic elements belonging to the group VIII in the periodic table of elements, such as rhodium, ruthenium, iridium and cobalt.

Examples of the heterogeneous catalysts for use in the present invention are platinum compounds, Raney nickel catalysts, and catalysts constructed in such a fashion that platinum, palladium, rhodium or ruthenium is supported by activated carbon, alumina or barium sulfate.

In the present invention, the above-mentioned heterogeneous catalysts are preferable from the viewpoint of the convenience of after-treatment.

When the heterogeneous catalyst is employed in the reaction, the reduction is initiated by vigorously stirring the compound, with the atmosphere replaced with hydrogen gas of 1 atm., in a closed system. The hydrogen gas is supplied to the reaction system through a pressure reducing valve, as absorbed in the course of the reaction. When the stoichiometric amount of the hydrogen gas is absorbed by the above dinitro compound, the absorption is terminated, and the reduction is completed. The reaction may be carried out at room temperature. In the case where the hydrogen gas is not readily absorbed by the dinitro compound, the system may be heated in the course of the reduction.

Examples of the reaction solvent in hydrogenation are methanol, ethanol, propanol, tetrahydrofuran, dioxane and ethyl acetate.

Alternatively, the reduction of the dinitro compound may be carried out by heating the dinitro compound together with a reducing agent such as iron-hydrochloric acid or stannous chloride-hydrochloric acid in an organic solvent. In such a case, it is preferable that the reaction temperature be set in the range of 70° C. to 120° C. The reduction reaction is generally terminated in about 0.5 to 3 hours. In the case where iron-hydrochloric acid is used as the reducing agent in the above reaction, the reaction is preferably carried out in N,N-dimethylformamide.

The triamine compounds of formula (I)-C can be obtained by allowing the above prepared diamino compound of formula (I)-B with a halobenzene compound of formula (IV) in the following reaction scheme:

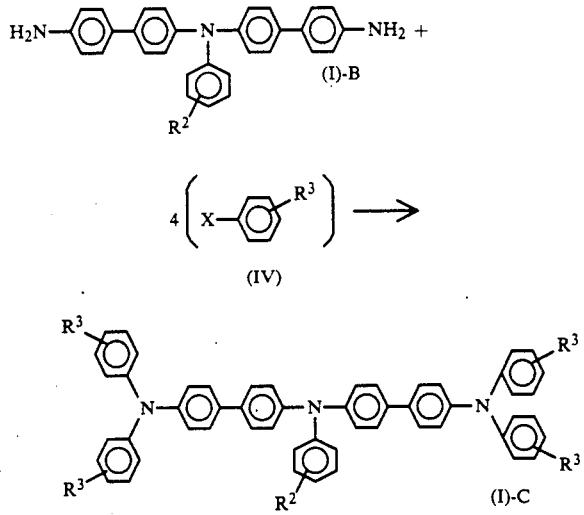

In the above formulas, X is a halogen, $R^2$ is hydrogen or an alkyl group having 1 to 6 carbon atoms, and $R^3$ represents hydrogen or an alkyl group having 1 to 6 carbon atoms.

In the formula (I)-C, examples of the alkyl group having 1 to 6 carbon atoms represented by $R^2$ and $R^3$ are a methyl group, an ethyl group, a propyl group and a butyl group. In the formula (IV), examples of a halogen represented by X are iodine, bromine and chlorine.

More specifically, the above diamino compound of formula (I)-B is allowed to react with the halobenzene compound of formula (IV) in the presence of copper powder, copper oxide or halogenated copper and an alkali with or without a solvent. The reaction is carried out at 150° C. to 250° C. in a stream of nitrogen, whereby the triamine compound of formula (I-C) can be obtained.

The above-mentioned alkali is added to the reaction mixture in a sufficient amount to neutralize hydrogen halogenide generated in the condensation reaction. Examples of the above alkali for use in the present invention are sodium hydroxide, potassium hydroxide, sodium carbonate and potassium carbonate.

Specific examples of the solvent for use in the above reaction are nitrobenzene, dichlorobenzene, quinoline, N,N-dimethylformamide, dimethyl sulfoxide, N-methylpyrrolidone and 1,3-dimethyl-2-imidazolidinone.

The above-mentioned triamine compounds having formula (I)-C according to the present invention are remarkably useful as photoconductive materials in the electrophotographic photoconductor and optically or chemically sensitized with a sensitizer such as a dye or a Lewis acid. In addition, triamine compounds having formula (I)-C effectively function as charge transporting materials in a function-separating type electrophotographic photoconductor where an organic or inorganic pigment serves as a charge generating material.

Specific examples of the previously mentioned sensitizer for use in the present invention are triarylmethane dyes such as Methyl Violet and Crystal Violet; xanthene dyes such as Rose Bengale, Erythrosin and Rhodamine; thiazine dyes such as Methylene Blue; and 2,4,7-trinitro-9-fluorenone and 2,4-dinitro-9-fluorenone.

Specific examples of the organic pigment serving as a charge generating material in the electrophotographic photoconductor for use in the present invention are azo pigments such as C.I. Pigment Blue 25 (C.I. 21180), C.I. Pigment Red 41 (C.I. 21200) and C.I. Pigment Red 3 (C.I. 45210); phthalocyanine pigments such as C.I. Pigment Blue 16 (C.I. 74100); indigo pigments such as C.I. Vat Brown 5 (C.I. 73410) and C.I. Vat Dye (C.I. 73030); and perylene pigments such as Algol Scarlet B and Indanthrene Scarlet R (made by Bayer Co., Ltd.). In addition to the above, inorganic pigments such as selenium, selenium-tellurium, cadmium sulfide and α-silicone can be employed.

The present invention will now be explained in more detail with reference to the following examples, which are given for illustration of the invention and are not intended to be limiting thereof.

EXAMPLE 1-1

Preparation of
N,N-bis{4'-nitro(1,1'-biphenyl)-4-yl}p-toluidine 150 ml of nitrobenzene was added to a mixture of 26.01 g (0.08 mol) of 4'-iodo-4-nitro(1,1'-biphenyl), 4.29 g (0.04 mol) of p-toluidine, 0.25 g of copper powder and 16.59 g of potassium carbonate. This mixture was dehydrated by azeotropy in a stream of nitrogen using an esterification tube, with stirring at 211° C. for 18 hours.

After the completion of dehydration, the mixture was cooled to room temperature and filtered through Celite.

The nitrobenzene was distilled away from the above obtained filtrate under reduced pressure to obtain a residue. The thus obtained residue was extracted with chloroform. The extract was washed with water, dried over magnesium sulfate, and then concentrated under reduced pressure, whereby a dark brown solid was obtained.

The thus obtained solid reaction product was subjected to column chromatography using silica gel as a carrier and toluene as a developing solvent, and then recrystallized from a mixed solvent of ethanol and toluene. Thus, 10.07 g of N,N-bis{4'-nitro(1,1'-biphenyl)-4-yl}p-toluidine having the following formula was obtained in the form of red needles in a 50.2% yield.

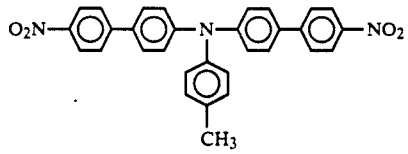

The melting point of the above obtained N,N-bis{4'-nitro(1,1'-biphenyl)-4-yl}p-toluidine was 221.5° C. to 222.5° C.

The results of the elemental analysis of the above product were as follows:

|  | % C | % H | % N |
| --- | --- | --- | --- |
| Calculated | 74.24 | 4.62 | 8.38 |
| Found | 74.18 | 4.63 | 8.23 |

FIG. 1 shows an infrared absorption spectrum of the above obtained N,N-bis{4'-nitro(1,1'-biphenyl)-4-yl}p-toluidine, taken by use of a KBr tablet, which indicates an absorption at 1510 cm$^{-1}$ and 1340 cm$^{-1}$ characteristic of stretching vibration of a nitro group.

EXAMPLE 1-2

Preparation of
N,N-bis{4'-amino(1,1'-biphenyl)-4-yl}p-toluidine 7.09 g of N,N-bis{4'-nitro(1,1'-biphenyl)-4-yl}-p-toluidine obtained in Example 1-1 was dissolved in 140 ml of tetrahydrofuran. The thus obtained solution was reduced with addition thereto of 0.71 g of 5% palladium-calcium, with hydrogen of 1 atom applied thereto at 18° C. in a shaking-type hydrogenation apparatus.

After the completion of reduction, the reaction mixture was filtered through Celite and the thus obtained filtrate was concentrated under reduced pressure, whereby pale pink powder was obtained.

The thus obtained reaction product was refluxed with stirring together with methanol and then water, so that 5.11 g of N,N-bis{4'-amino(1,1'-biphenyl)-4-yl}-p-toluidine having the following formula was obtained in the form of pale pink powder in an 81.9%.

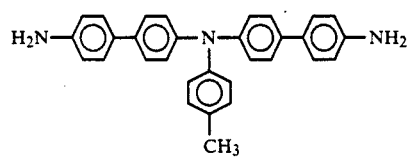

According to the DSC measurement, the thus obtained N,N-bis{4'-amino(1,1'-biphenyl)-4-yl}-p-toluidine showed an endothermic curve with a peak in the range from at 108° C. to 115° C. connected to a broad peak at 126° C.

The results of the elemental analysis of the above product were as follows:

|  | % C | % H | % N |
| --- | --- | --- | --- |
| Calculated | 84.32 | 6.16 | 9.52 |
| Found | 84.58 | 6.35 | 9.48 |

The above calculation was based on the formula for N,N-bis{4'-amino(1,1'-biphenyl)-4-yl}-p-toluidine of $C_{31}H_{27}N_3$.

Figure 2:
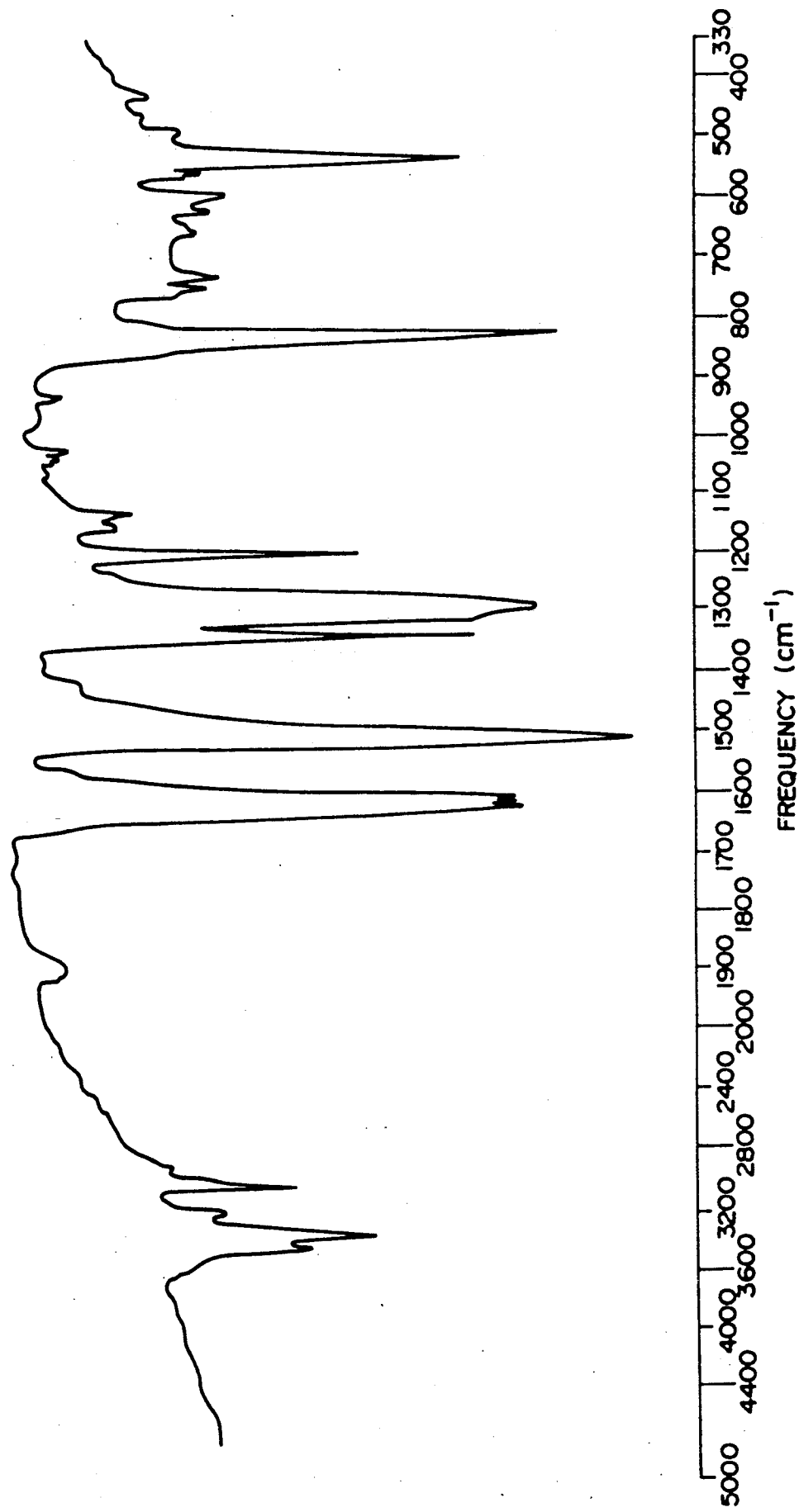

FIG. 2 shows an infrared absorption spectrum of the above obtained N,N-bis{4'-amino(1,1'-biphenyl)-4-yl}-p-toluidine, taken by use of a KBr tablet, which indicates an absorption at 3460 cm$^{-1}$ and 3380 cm$^{-1}$ characteristic of stretching vibration of primary amine.

EXAMPLE 1-3

Preparation of
N,N-bis{4'-nitro(1,1'-biphenyl)-4-yl}aniline

The procedure for preparation of N,N-bis{4'-nitro(1,1'-biphenyl)-4-yl}-p-toluidine in Example 1-1 was repeated except that p-toluidine employed in Example 1-1 was replaced by aniline, whereby N,N-bis{4'-nitro(1,1'-biphenyl)-4-yl}aniline having the following formula was obtained in the form of red needles.

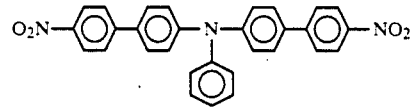

The melting point of the above obtained N,N-bis{4'-nitro(1,1'-biphenyl)-4-yl}aniline was 276.0° C. to 277.0° C.

The results of the elemental analysis of the above product were as follows:

|  | % C | % H | % N |
| --- | --- | --- | --- |
| Calculated | 73.91 | 4.34 | 8.62 |
| Found | 74.06 | 4.16 | 8.54 |

The above calculation was based on the formula for N,N-bis{4'-nitro(1,1'-biphenyl)-4yl}aniline of $C_{30}H_{21}N_3O_4$.

Figure 3:
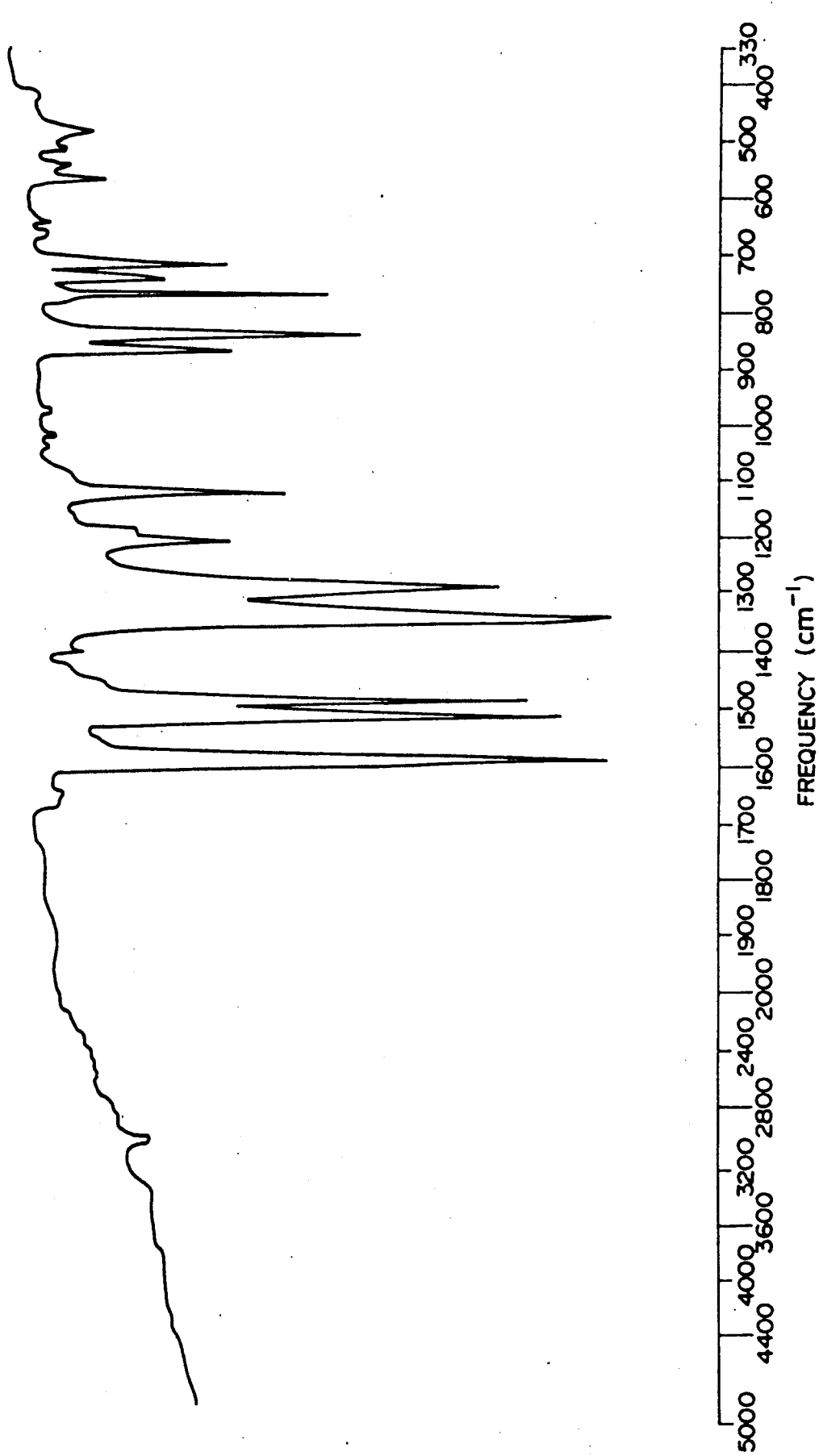

FIG. 3 shows an infrared absorption spectrum of the above obtained N,N-bis{4'-nitro(1,1'-biphenyl)-4-yl}aniline, taken by use of a KBr tablet.

EXAMPLE 1-4

Preparation of
N,N-bis{4'-amino(1,1'-biphenyl)-4-yl}aniline

The procedure for preparation of N,N-bis{4'-amino(1,1'-biphenyl)-4-yl}-p-toluidine in Example 1-2 was repeated except that N,N-bis{4'-nitro(1,1'-biphenyl)-4-yl}-p-toluidine employed in Example 1-2 was replaced by N,N-bis{4'-nitro(1,1'-biphenyl)-4-yl}aniline obtained in Example 1-3, whereby N,N-bis{4'-amino(1,1'-biphenyl)-4-yl}aniline having the following formula was obtained in the form of light gray powder.

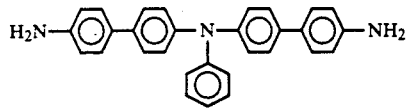

The melting point of the above obtained N,N-bis{4'-amino(1,1'-biphenyl)-4-yl}aniline was 230.5° C. to 231.5° C.

The results of the elemental analysis of the above product were as follows:

|  | % C | % H | % N |
|---|---|---|---|
| Calculated | 84.28 | 5.89 | 9.83 |
| Found | 84.45 | 5.84 | 9.97 |

The above calculation was based on the formula for N,N-bis{4'-amino(1,1'-biphenyl)-4-yl}aniline of $C_{30}H_{25}N_3$.

Figure 4:
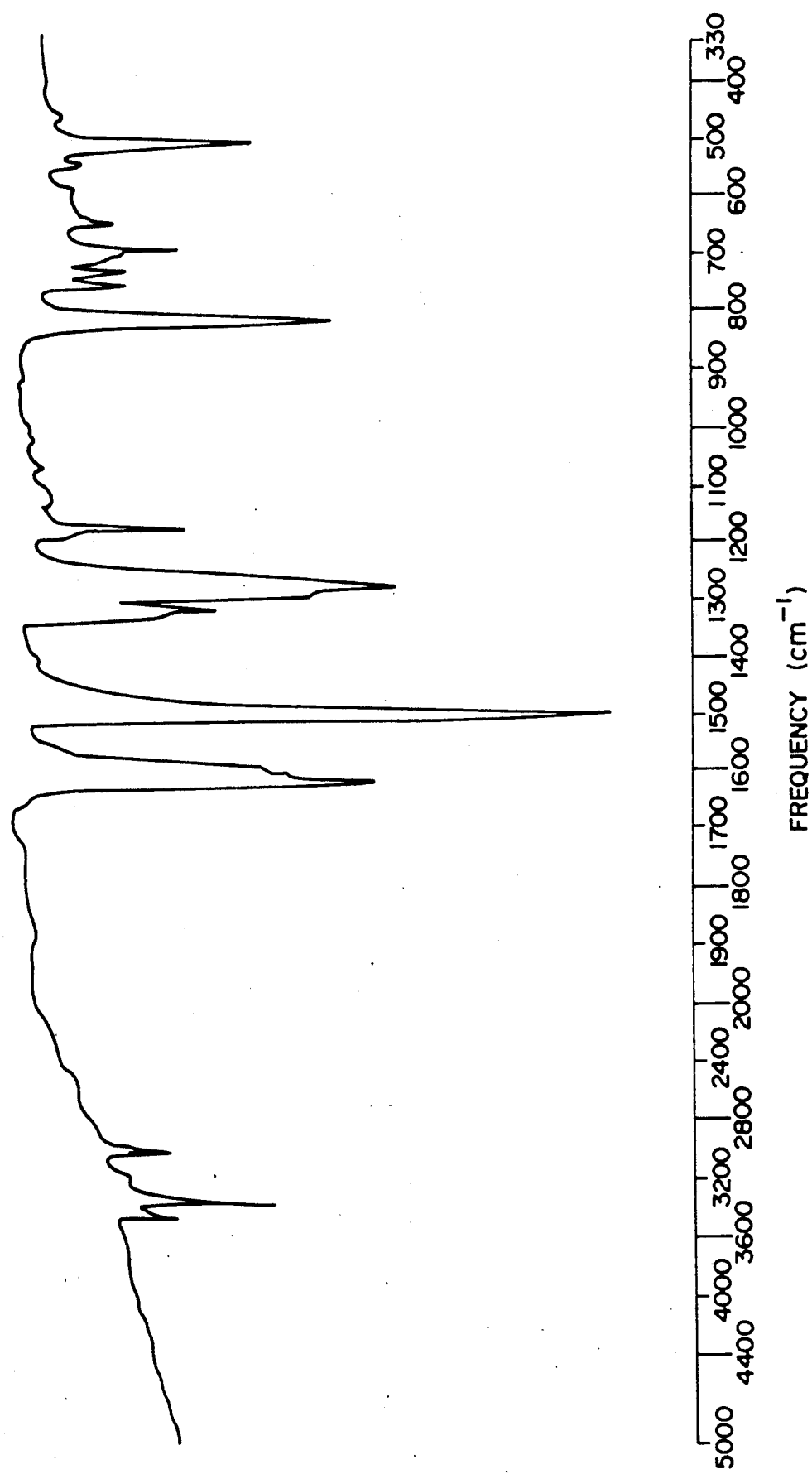

FIG. 4 shows an infrared absorption spectrum of the above obtained N,N-bis{4'-amino(1,1'-biphenyl)-4-yl}aniline, taken by use of a KBr tablet.

EXAMPLE 2-1

A mixture of 1.77 g (4.00 mmol) of N,N-bis{4'-amino-(1,1'-biphenyl)-4-yl}-p-toluidine obtained in Example 1-2, 26.11 g (0.128 mol) of 4-iodobenzene, 0.25 g of copper powder and 4.42 g of potassium carbonate was dehydrated by azeotropy in a stream of nitrogen, using an esterification tube, with stirring at 182° C. to 183° C. for 10 hours.

After the completion of dehydration, the mixture was cooled to room temperature and filtered through Celite.

To the filtrate thus obtained, chloroform was added and a resultant chloroform layer was washed with water and dried over magnesium sulfate, and then concentrated under reduced pressure, whereby a dark brown oily substance was obtained.

The thus obtained reaction product was subjected to column chromatography using silica gel as a carrier and a mixed solvent of toluene and n-hexane with a mixing ratio of 1:1 as a developing solvent, and then recrystallized from ethyl acetate. Thus, 0.87 g of triamine compound having the following formula was obtained in the form of light yellow needles in a 29.2% yield.

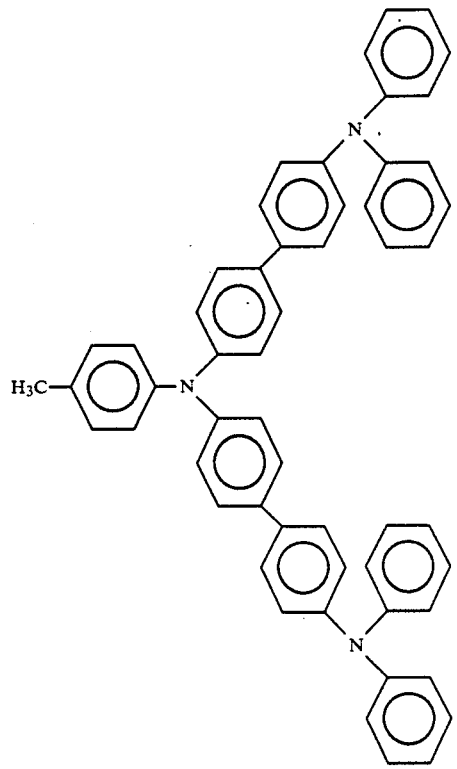

The results of the elemental analysis of the above triamine compound were as follows:

|  | % C | % H | % N |
|---|---|---|---|
| Calculated | 88.56 | 5.81 | 5.63 |
| Found | 88.68 | 5.80 | 5.52 |

The above calculation was based on the formula for the triamine compound of $C_{55}H_{43}N_3$.

Figure 5:
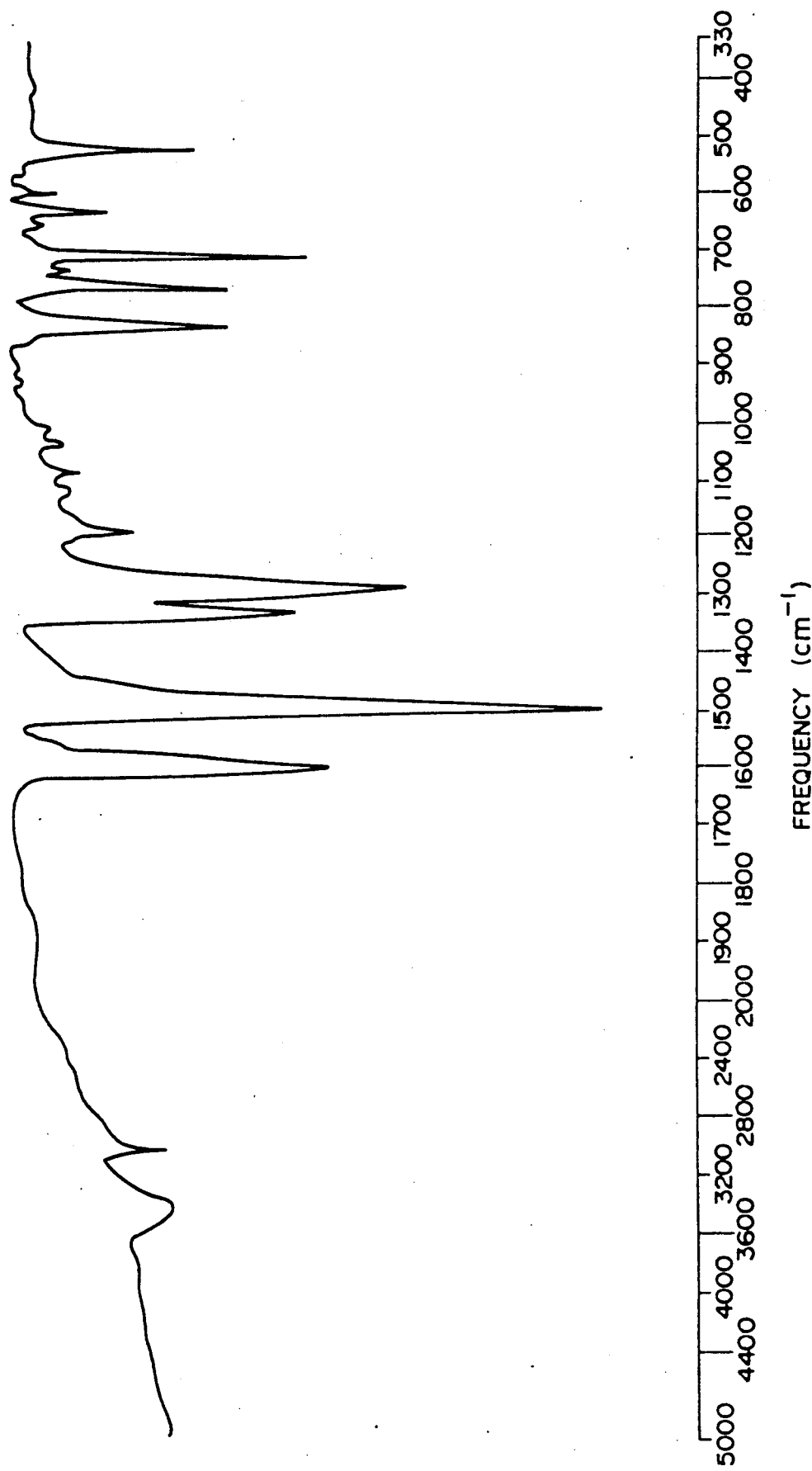
FIGS. 5 to 7 are the infrared absorption spectra of triamine compounds according to the present invention.
Figure 8:
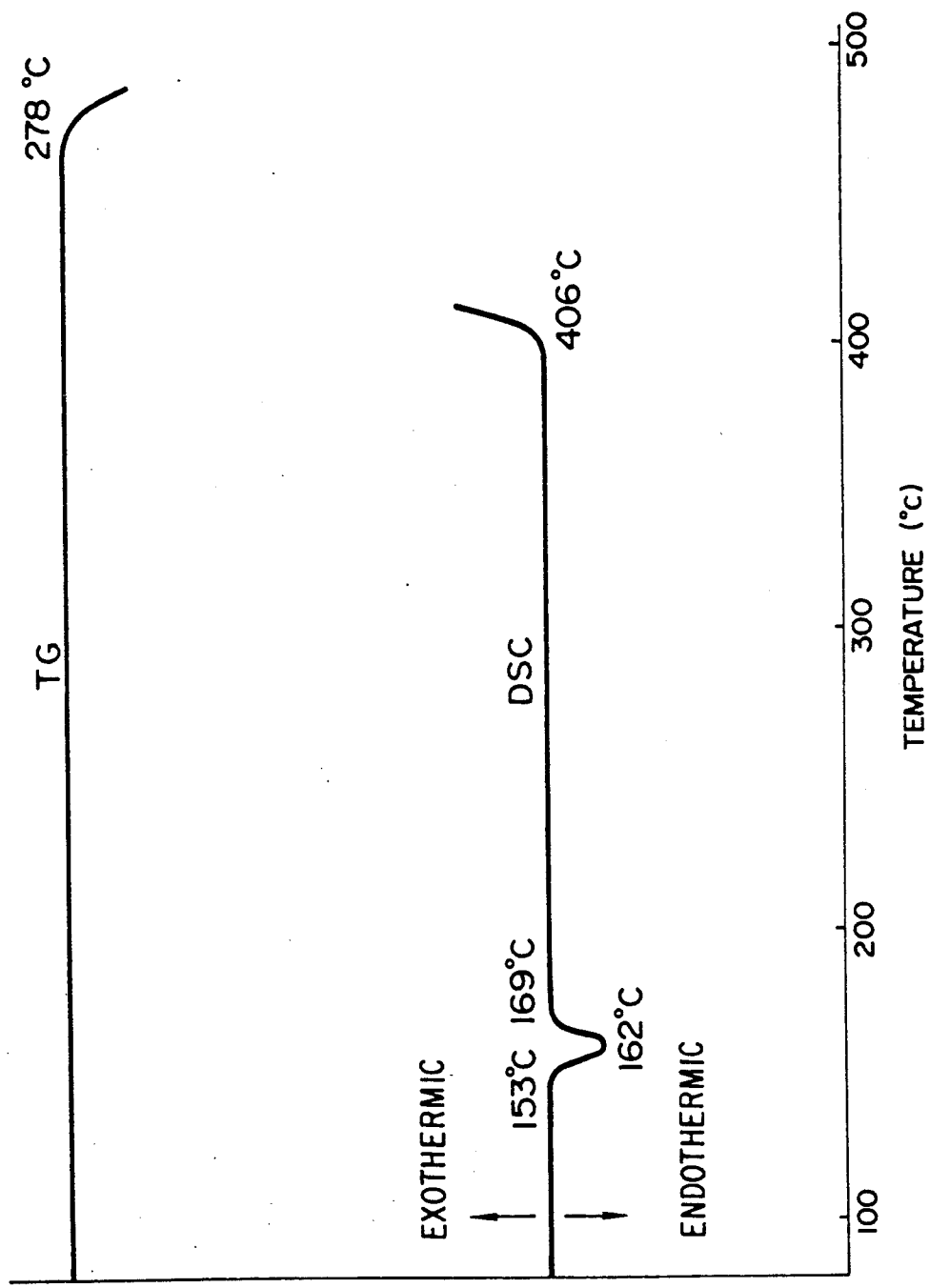
FIG. 8 is a graph showing the results of a thermal analysis of a triamine compound according to the present invention.

FIG. 5 shows an infrared absorption spectrum of the above triamine compound, taken by use of a KBr tablet. In addition, FIG. 8 shows the results of thermal analysis (TG and DSC) thereof.

EXAMPLE 2-2

The procedure for preparation of the triamine compound in Example 2-1 was repeated except that N,N-bis{4'-amino(1,1'-biphenyl)-4-yl}-p-toluidine employed in Example 2-1 was replaced by N,N-bis{4'-amino(1,1'-biphenyl)-4-yl}aniline obtained in Example 1-4, whereby a triamine compound having the following formula was obtained.

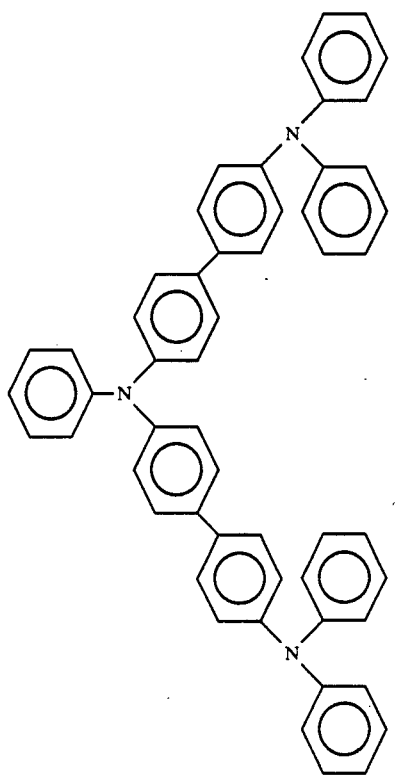

The melting point of the above obtained triamine compound was 195.0° C. to 196.5° C.

The results of the elemental analysis of the above triamine compound were as follows:

|  | % C | % H | % N |
|---|---|---|---|
| Calculated | 88.61 | 5.65 | 5.74 |
| Found | 88.67 | 5.41 | 5.80 |

Figure 6:
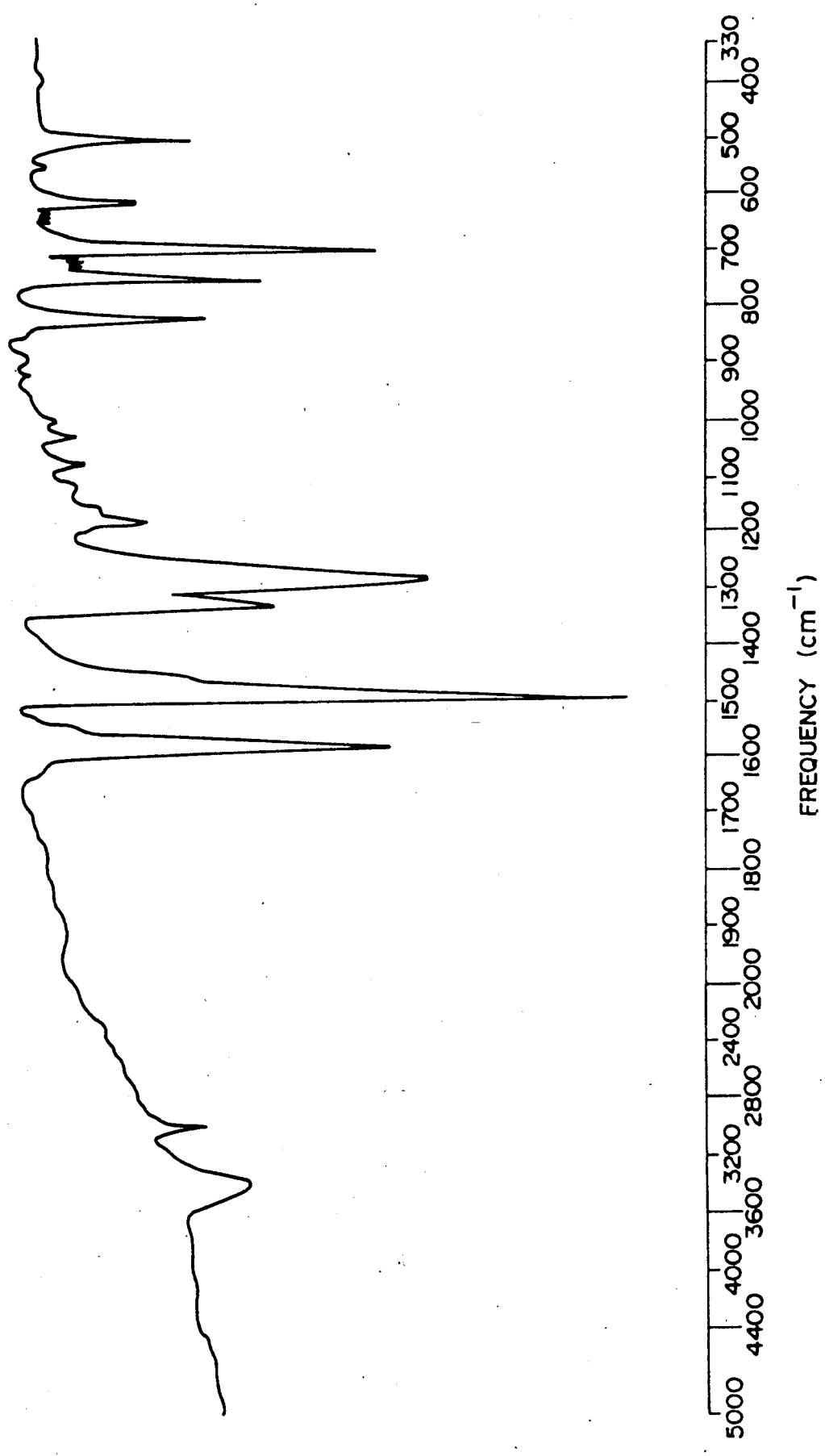

FIG. 6 shows an infrared absorption spectrum of the above obtained triamine compound, taken by use of a KBr tablet.

EXAMPLE 2-3

The procedure for preparation of the triamine compound in Example 2-1 was repeated except that 4-iodobenzene employed in Example 2-1 was replaced by p-iodotoluene, whereby a triamine compound having the following formula was obtained.

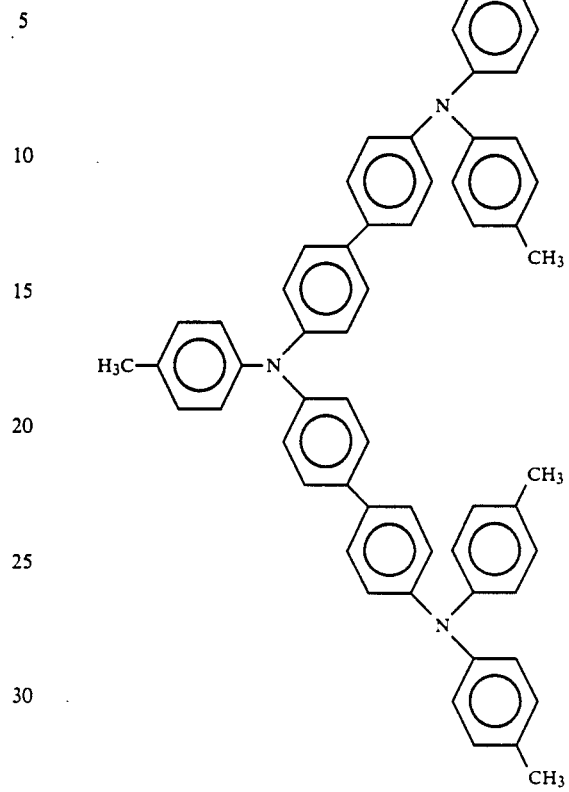

The results of the elemental analysis of the above triamine compound were as follows:

|  | % C | % H | % N |
|---|---|---|---|
| Calculated | 88.35 | 6.41 | 5.24 |
| Found | 88.50 | 6.29 | 5.08 |

Figure 7:
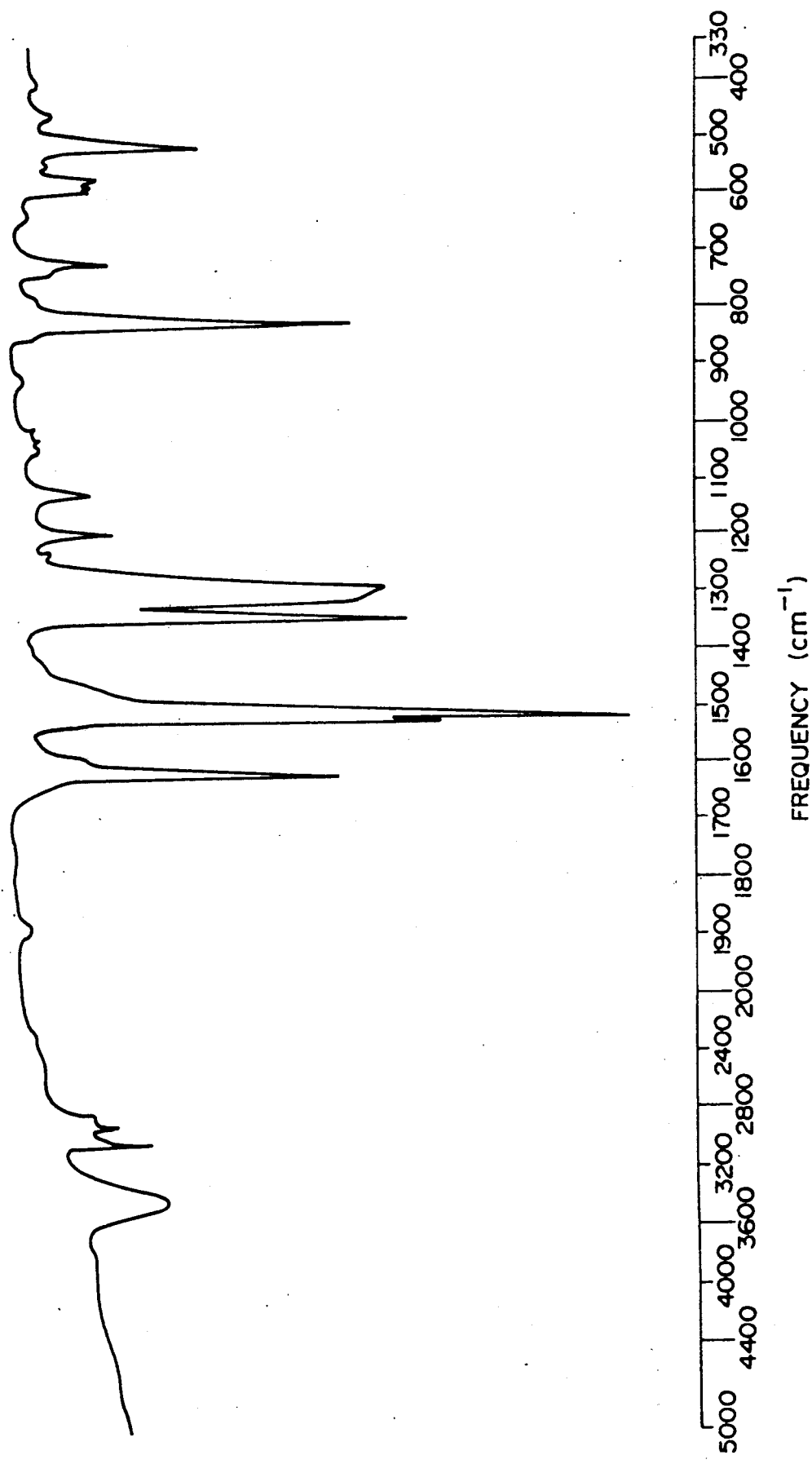

FIG. 7 shows an infrared absorption spectrum of the above obtained triamine compound, taken by use of a KBr tablet.

APPLICATION EXAMPLE 1

Preparation of Bisazo compound

N,N-bis{4'-amino(1,1'-biphenyl)-4-yl}-p-toluidine obtained in the above Example 1-2 was subjected to diazotization, so that a tetrazonium salt having the following formula (V) was obtained.

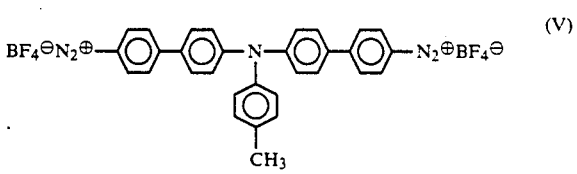

(V)

The above obtained tetrazonium salt of formula (V) was allowed to react with a coupler having formula (VI), whereby a bisazo compound having formula (VII) was obtained.

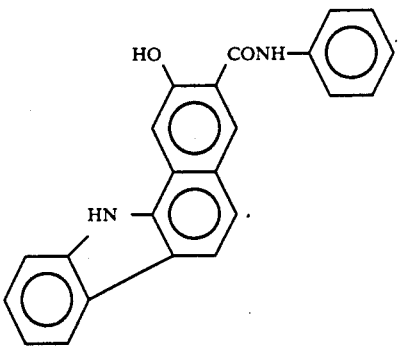

(VI)

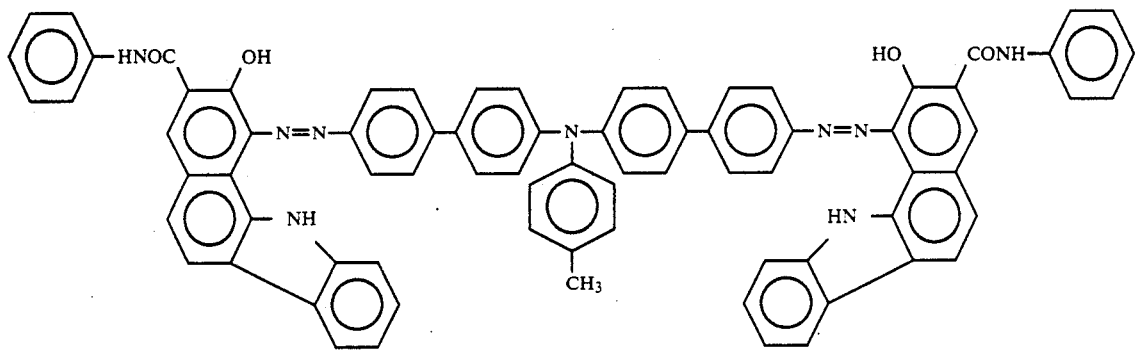

(VII)

Formation of Electrophotographic Photoconductor 7.5 parts by weight of the above prepared bisazo compound serving as a charge generating material and 500 parts by weight of 0.5% tetrahydrofuran solution of polyester resin, "Vylon 200" (Trademark), made by Toyobo Company, Ltd., were dispersed and ground in a ball mill. The thus prepared dispersion was coated on an aluminum surface of an aluminum-deposited polyester film by a doctor blade and dried at room temperature, so that a charge generation layer having a thickness of about 1 μm was formed on the aluminum-deposited polyester film.

2 parts by weight of 1-phenyl-3-(4-diethylaminostyryl)-5-(4-diethylaminophenyl)pyrazoline serving as a charge transporting material was dissolved in 10% tetrahydrofuran solution of polycarbonate resin, "Panlite K-1300" (Trademark), made by Teijin Limited., to prepare a solution. This solution was coated on the above formed charge generation layer by a doctor blade, and dried at 80° C. for 2 minutes and then at 120° C. for 5 minutes, so that a charge transport layer having a thickness of about 20 μm was formed on the charge generation layer. Thus, a two-layered type electrophotographic photoconductor was obtained.

To evaluate the photosensitivity of the thus obtained electrophotographic photoconductor in the visible light range, it was charged negatively in the dark under application of −6 kV of corona charge for 20 seconds, using a commercially available electrostatic copying sheet testing apparatus, "Paper Analyzer Model SP-428", made by Kawaguchi Electro Works Co, Ltd. The photoconductor was then allowed to stand in the dark for 20 seconds without applying any charge thereto, and the surface potential Vo (V) of the photoconductor was measured. The photoconductor was then illuminated by a tungsten lamp in such a manner that the illuminance on the illuminated surface of the photoconductor was 4.5 lux, and the exposure $E_{2/1}$ (lux·sec) required to reduce the initial surface potential Vo (V) to ½ the initial surface potential Vo (V) was measured. The results are as follows:

$Vo = -991$ (V)

$E_{\frac{1}{2}} = 1.41$ (lux·sec)

APPLICATION EXAMPLE 2

Formation of Electrophotographic Photoconductor 7.5 parts by weight of a bisazo compound having the following formula serving as a charge generating material and 500 parts by weight of 0.5% tetrahydrofuran solution of polyester resin, "Vylon 200" (Trademark), made by Toyobo Company, Ltd., were dispersed and ground in a ball mill.

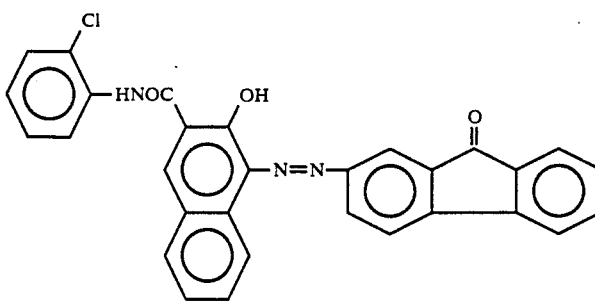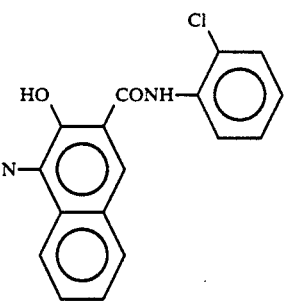

The thus prepared dispersion was coated on an aluminum surface of an aluminum-deposited polyester film by a doctor blade and dried at room temperature, so that a charge generation layer having a thickness of about 1 μm was formed on the aluminum-deposited polyester film.

One part by weight of the above prepared triamine compound obtained in Example 2-1 was dissolved in a resin solution which was prepared by mixing 1 part by weight of polycarbonate resin, "Panlite K-1300" (Trademark), made by Teijin Limited., with 8 parts by weight of tetrahydrofuran. This solution was coated on the above formed charge generation layer by a doctor blade, and dried at 80° C. for 2 minutes and then at 120° C. for 5 minutes, so that a charge transport layer having a thickness of about 20 μm was formed on the charge generation layer. Thus, a two-layered type electrophotographic photoconductor was obtained.

To evaluate the photosensitivity of the thus obtained electrophotographic photoconductor in the visible light range, it was charged negatively in the dark under application of −6 kV of corona charge for 20 seconds, using a commercially available electrostatic copying sheet testing apparatus, "Paper Analyzer Model SP-428", made by Kawaguchi Electro Works Co, Ltd. The surface potential Vm (V) of the photoconductor was measured. The photoconductor was then allowed to stand in the dark for 20 seconds without applying any charge thereto, and the surface potential Vo (V) of the photoconductor was measured. The photoconductor was then illuminated by a tungsten lamp in such a manner that the illuminance on the illuminated surface of the photoconductor was 4.5 lux, and the exposure $E_{2/1}$ (lux·sec) required to reduce the initial surface potential Vo (V) to ½ the initial surface potential Vo (V) was measured. Furthermore, the residual surface potential Vr (V) of the photoconductor was measured after illuminated by a tungsten lamp for 30 seconds. The results are given in Table 1.

COMPARATIVE APPLICATION EXAMPLE 1

The procedure for formation of the electrophotographic photoconductor in Application Example 2 was repeated except that the triamine compound used as a charge transporting material in Application Example 2 was replaced by 4,4',4"-trimethyltriphenylamine, whereby a comparative electrophotographic photoconductor was obtained.

The photosensitivity of the thus obtained comparative electrophotographic photoconductor was measured in the same manner as employed in Application Example 2. The results are given in Table 1.

TABLE 1

|  | Vm | Vo | Vr | E½ | State of C.T. Layer(*) |
|---|---|---|---|---|---|
| Application Example 2 | −1165 | −674 | 0 | 0.62 | Transparent |
| Comparative Application Example 1 | −1480 | −1287 | −129 | 1.24 | Opaque white |

(*)C.T. Layer denotes "charge transport layer".

As is apparent from the above description, dinitro compounds and diamino compounds according to the present invention are remarkably useful as starting or intermediate materials for preparing organic photoconductive materials which are used in electrophotographic photoconductors, particularly in two-layered type electrophotographic photoconductors.

In addition to the above, dinitro compounds and diamino compounds according to the present invention can be easily prepared by condensation reaction and reduction reaction, respectively. Those preparing methods of dinitro compounds and diamino compounds according to the present invention are considered to be industrially useful.

Furthermore, triamine compounds according to the present invention effectively serve as photoconductive materials. As previously mentioned, by being optically or chemically sensitized with a sensitizer such as a dye or a Lewis acid, triamine compounds according to the present invention appropriately function as charge transporting materials when contained in the photoconductive layer of the electrophotographic photoconductor, in particular, in the charge transport layer of the two-layered type electrophotographic photoconductor.

What is claimed is:

1. A compound having formula (I):

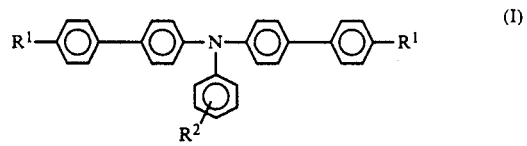

wherein $R^1$ is a nitro group, an amino group or a diphenylamino group which may have a substituent; and $R^2$ is hydrogen or an alkyl group having 1 to 6 carbon atoms.

2. The compound as claimed in claim 1, wherein $R^1$ in said formula (I) is a nitro group.

3. The compound as claimed in claim 1, wherein $R^1$ is a nitro group and $R^2$ is hydrogen or a methyl group in said formula (I).

4. The compound as claimed in claim 1, wherein $R^1$ is a nitro group and $R^2$ is hydrogen or a methyl group at a para position with respect to N in said formula (I).

5. The compound as claimed in claim 1, wherein $R^1$ in said formula (I) is an amino group.

6. The compound as claimed in claim 1, wherein $R^1$ is an amino group and $R^2$ is hydrogen or a methyl group in said formula (I).

7. The compound as claimed in claim 1, wherein $R^1$ is an amino group and $R^2$ is hydrogen or a methyl group at a para position with respect to N in said formula (I).

8. The compound as claimed in claim 1, wherein $R^1$ in said formula (I) is a diphenylamino group of formula:

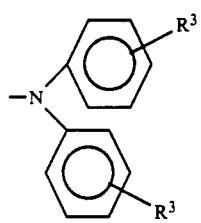

wherein $R^3$ is hydrogen or an alkyl group having 1 to 6 carbon atoms.

9. The compound as claimed in claim 1, wherein $R^1$ in said formula (I) is

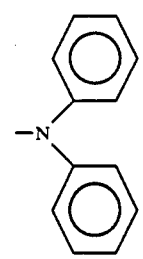

and $R^2$ in said formula (I) is hydrogen or a methyl group.

10. The compound as claimed in claim 1, wherein $R^1$ in said formula (I) is

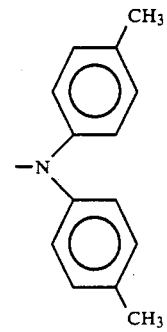

and $R^2$ in said formula (I) is hydrogen or a methyl group.

* * * * *